United States Patent [19]

Jackson, III et al.

[11] Patent Number: 4,813,064
[45] Date of Patent: Mar. 14, 1989

[54] METHOD AND APPARATUS FOR COUNTERBALANCING ROTATING BODIES

[76] Inventors: David Jackson, III, 1126 Moneta Ave., Aurora, Ohio 44202; Dale A. Havel, 11631 Lyman Dr., Chesterland, Ohio 44026

[21] Appl. No.: 12,178

[22] Filed: Feb. 9, 1987

[51] Int. Cl.⁴ .......................................... G01N 21/34
[52] U.S. Cl. ................... 378/197; 378/193; 248/572
[58] Field of Search ............... 378/197, 196, 195, 194, 378/193, 21, 22; 248/572, 123, 325, 292.1

[56] References Cited

U.S. PATENT DOCUMENTS

| Re. 32,164 | 5/1986 | Kruger. | |
|---|---|---|---|
| 476,739 | 6/1892 | Flaherty | 248/292.1 |
| 2,168,209 | 8/1939 | Haupt | 248/572 |
| 2,471,998 | 5/1949 | Berggren | 248/572 |
| 2,640,159 | 5/1953 | Gerneth | 378/194 |
| 2,876,362 | 3/1959 | Foderaro | 378/194 |
| 3,902,070 | 8/1975 | Amor, Jr. et al. | |
| 4,439,003 | 3/1984 | Roth | 248/123.1 |
| 4,626,688 | 12/1986 | Barnes. | |

FOREIGN PATENT DOCUMENTS 1052631 3/1959 Fed. Rep. of Germany ...... 378/194

OTHER PUBLICATIONS

Tesic, M. M. et al.; "Digital Radiography of the Chest: Design Features and Considerations for a Prototype Unit", Radiology, vol. 148, No. 1, pp. 259-264, Jul. 1983.
Capp, M. P. et al.; "Photo Electronic Radiology Department", S.P.I.E. vol. 314, Digital Radiography 1981, pp. 2-7.

Picker International Installation Manual No. T55D-032 for Apollo Tubestand dated Jan. 31, 1983.

Primary Examiner—Carolyn E. Fields
Assistant Examiner—Joseph A. Hynds

[57] ABSTRACT

A diagnostic imaging scanner system is provided which includes an arm structure mounted to a support structure for pivotal motion about a substantially horizontal arm axis. A source of radiation directs radiation along a beam path. A detector is mounted on the arm structure in alignment with the beam path and is spaced from the source to accommodate placement of a subject under examination therebetween. During pivotal motion the detector thus moves along an arcuate path which lies in a substantially vertical plane. Means are provided for compensating the gravitational torque experienced about the arm axis during scanning motion. The compensating means includes means for producing a predetermined force and a cam mounted for pivotal motion about a substantially horizontal cam axis which is operatively coupled to the force means for converting the predetermined force to a first torque about the cam axis. Means are provided for rotatively coupling the cam to the arm strucure such that the first torque is transferred to a second torque about said arm axis. The second torque is substantially equal and opposite to the gravitational torque about the arm axis during scanning motion. The predetermined force means can include either a spring or a weight suspended against gravity. The cam defines a profile having a monotonically varying radius about its operative extent. The cam radius varies sinusoidally over its operative extent. Additionally, the cam profile may be further modified to take into account variations in the spring constant over the range of spring operation.

21 Claims, 2 Drawing Sheets

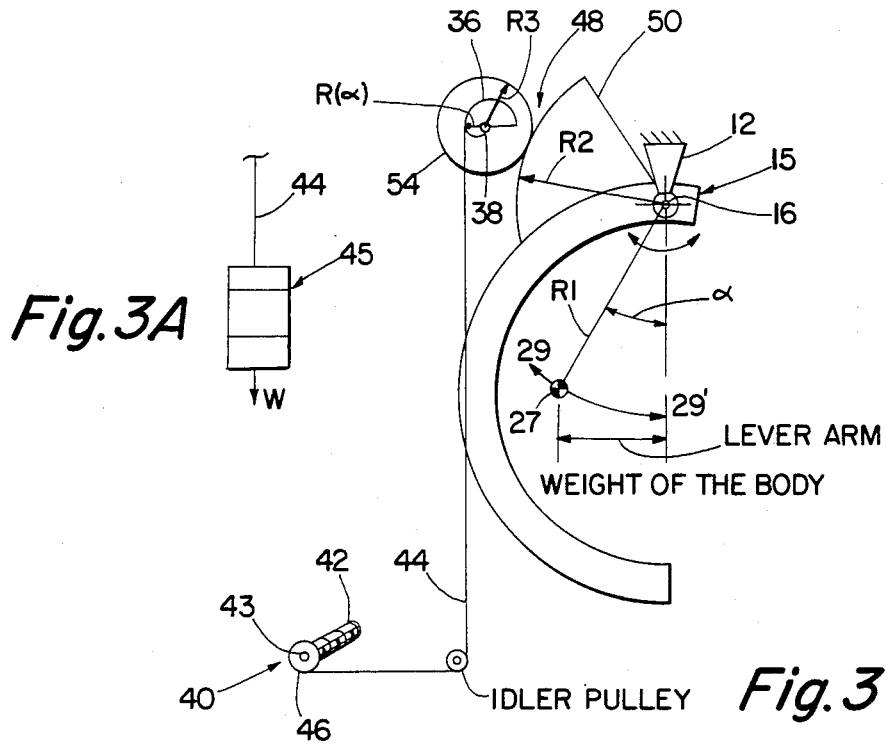
*Fig.3A*
*Fig.3*
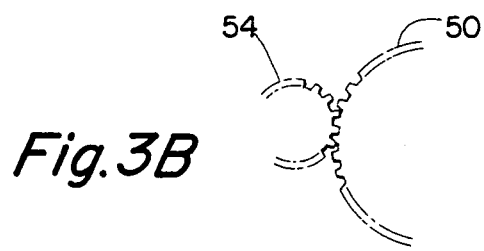
*Fig.3B*
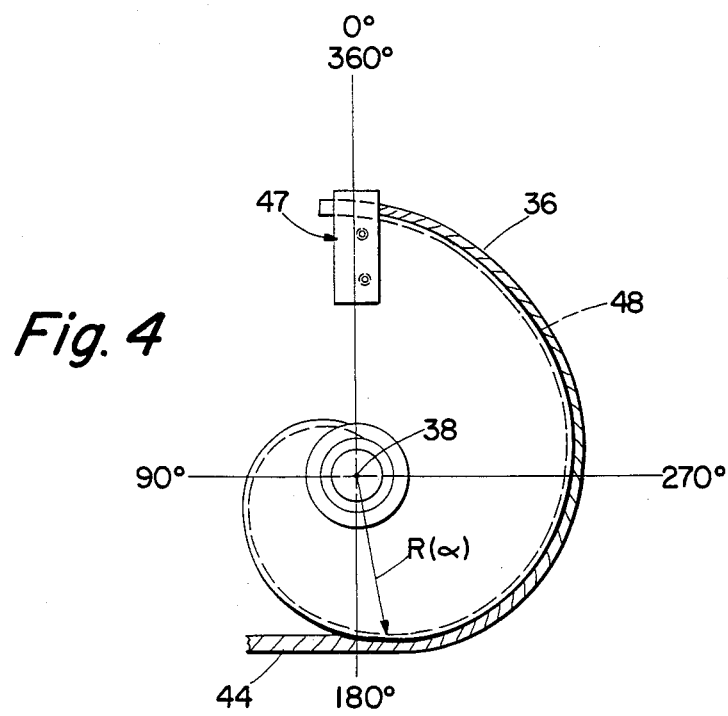
*Fig.4*

METHOD AND APPARATUS FOR COUNTERBALANCING ROTATING BODIES

TECHNICAL FIELD

This invention relates to the field of medical diagnostic imaging and more particularly to an improved method and apparatus especially suited for use in rotating diagnostic equipment for facilitating scanning motion and controlling scanning speed.

BACKGROUND ART

In a conventional radiographic system, an x-ray source is actuated to direct a divergent area beam of x-rays through a patient. A cassette containing an x-ray sensitive screen and light and x-ray sensitive film is positioned in the x-ray path on a side of the patient opposite the source. Radiation passing through the patient's body is attenuated to varying degrees in accordance with the various types of tissue through which the x-rays pass. The attenuated x-rays emerge from the patient in a pattern and strike the phosphor screen which in turn exposes the film. The x-ray film is processed to yield a visible image which can be interpreted by a radiologist as defining internal body structure and/or condition of the patient.

In conventional systems of the type described above the x-ray source is mounted to a support structure. Such structure is commonly a ceiling supported, telescoping carriage which permits selection of various source to film distances. The weight of the source and associated componentry are counterbalanced against gravity via a spring motor and a cable/pulley arrangement. A support cable take-up drum or cam is provided to compensate for the variance in the spring tension force over the operative range of spring extension. The take-up drum is provided with a helical groove which receives the support cable. By decreasing the support cable drum take-up radius as the counterbalance springs are extended, a substantially constant counterbalance force is applied to the support cable. Further details of the above described counterbalance system can be found in U.S. Pat. No. 3,902,070 to Amor Jr. et al. which is owned by the present assignee.

It is to be noted that the above described counterbalance system is useful where the center of gravity of the moving component moves in a substantially vertical, straight line.

More recently, digital radiography techniques have been developed. In digital radiography, the source directs radiation through a patient's body to a detector in the beam path beyond the patient. The detector, by use of appropriate sensor means, responds to the incident radiation image to produce analog signals representing the sensed radiation, which signals are converted to digital information and fed to a digital data processing unit. The data processing unit records, and/or processes and enhances the digital data. A display unit responds to the appropriate digital data representing the image to convert the digital information back into analog form and produce a visual display of the patient's internal body structure.

Digital radiography includes radiographic techniques in which a thin spread beam of x-rays is used. In this technique, often called "scan" (or slit) projection radiography (SPR), a spread beam of x-rays are scanned across the patient's body, or the patient is movably interposed between the source and an array of individual cellular detector segments. In such an embodiment, relative movement is effected between the source/detector arrangement and the patient's body, keeping the detector aligned with the beam, such that a large area of the patient's body is scanned by the beam of x-rays.

One such SPR system is described in more detail in U.S. Pat. 4,626,688 to Barnes entitled Split Energy Level Radiation Detection and in the following publication:

Tesic, M. M. et al.; "Digital Radiography of the Chest: Design Features and Considerations For a Prototype Unit", Radiology, Vol. 148 No. 1, pp 259–64, July 1983.

The above described SPR Systems are configured such that the scanning motion is about a substantially vertical axis, i.e., the detector moves along a path defining an arc lying substantially in a horizontal plane.

It has also been proposed to provide an SPR system wherein the scanning motion is about a substantially horizontal axis thereby causing the detector to move along a path defining an arc lying substantially in a vertical plane.

In both configurations the scanning motion is provided by means of electromechanical servo-systems driven by controllable electric motors. An encoder is utilized to provide a closed loop feedback system wherein motor performance is adjusted in accordance with the sensed location of the detector.

In the second system wherein the scanning motion is about a horizontal axis, a difficulty is encountered in that the center of gravity of the rotating body rotates about the pivot point. The torque required to effect scanning motion about the pivot axis varies sinusoidally. A electromechanical servo system designed to compensate for the torque variations would be unduly complex. Further, a motor able to provide sufficient torque to overcome the system torque at the extremes of the scan motion would be large and prohibitively expensive.

It is therefore an object of this invention to provide a lightweight, reliable, simple and inexpensive counterbalance system which compensates for gravitation torques experienced in a system which rotates about a substantially horizontal axis thereby permitting the use of less costly and complex drive components.

DISCLOSURE OF THE INVENTION

The disadvantages and problems of the prior art are reduced or eliminated by provision of a diagnostic imaging scanner system including an arm structure mounted to a support structure for pivotal motion about a substantially horizontal arm axis. A source of radiation directs radiation along a beam path. A detector is mounted on the arm structure in alignment with the beam path and is spaced from the source to accommodate placement of a subject under examination therebetween. During pivotal motion the detector thus moves along an arcuate path which lies in a substantially vertical plane. Means are provided for compensating the gravitational torque experienced about the arm axis during scanning motion.

In a more limited aspect of the present invention, the compensating means includes means for producing a predetermined force and a cam mounted for pivotal motion about a substantially horizontal cam axis. The cam is operatively coupled to the force means for converting the predetermined force to a first torque about the cam axis. Means are provided for rotatively coupling the cam to the arm structure such that the first torque is transferred to a second torque about the arm axis. The second torque is substantially equal and opposite to the gravitational torque about the arm axis during scanning motion.

In yet a further aspect of the present invention, the cam defines a profile having a monotonically varying radius about its operative extent. Additionally, the predetermined force means can include either a spring or a weight suspended against gravity.

In still yet another aspect of the present invention, the cam radius varies sinusoidally over its operative extent. The cam profile can be further modified to take into account variations in the spring force over the range of operation.

One advantage of the present invention is that it provides a counterbalance to rotating structure without adding counterweight to the overall system weight, and without adding any significant inertial load to the scan drive.

Another advantage of the present invention is that it provides a counterbalance system capable of producing a counterbalance force that varies as a function of scanning motion.

Yet another advantage of the present invention is that it provides an inexpensive, simple and lightweight means of balancing rotating bodies in order that the drive motor remains under substantially constant load during scanning motion.

These and still other advantages will become apparent to those of ordinary skill in the art upon reading and understanding the following detailed description of the preferred embodiment.

BRIEF DESCRIPTION OF THE DRAWINGS

The invention may be embodied in various steps and arrangement of steps and components and arrangement of components. The drawings are only for purposes of illustrating a preferred embodiment and are not to be construed as limiting the invention.

FIG. 3 is a schematic representation of the counterbalance mechanism of the present invention.

FIG. 3A is a schematic representation of a alternate embodiment of the present invention. FIG. 3B is a detail view of a portion of the counterbalance mechanism of the resent invention.

FIG. 4 is a frontal view of the cam incorporated in the present invention.

BEST MODE FOR CARRYING OUT THE INVENTION

Figure 1:
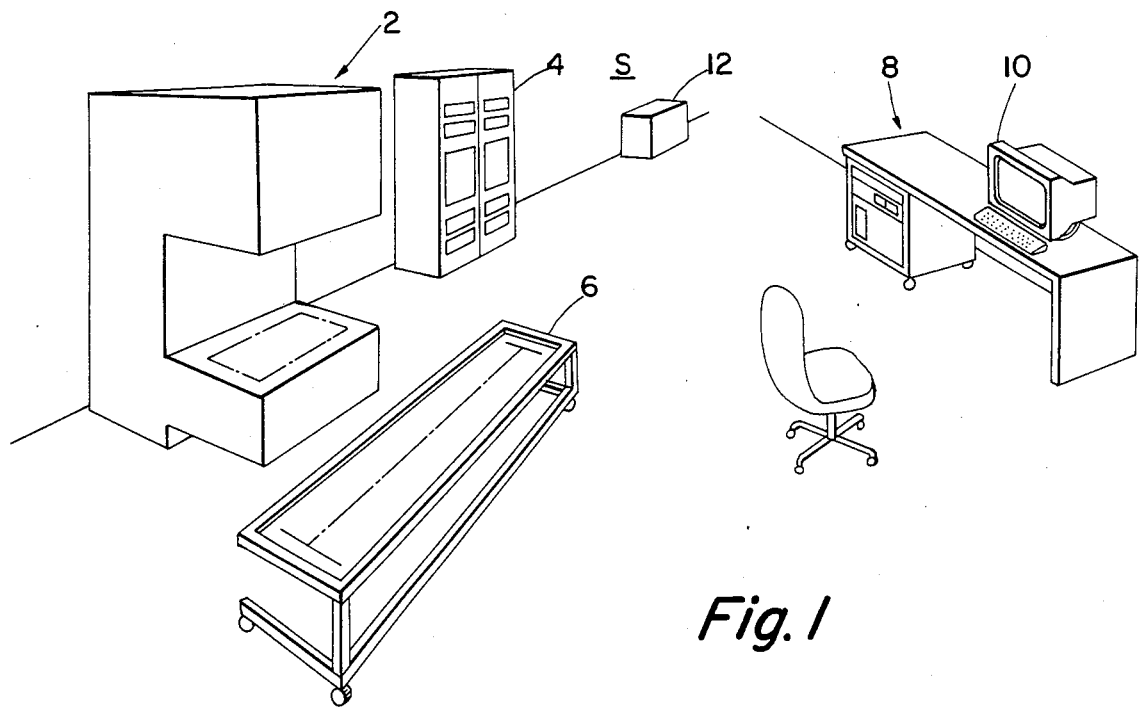
FIG. 1 is a perspective view of a slit projection type digital radiography system in which the present invention is incorporated.

FIG. 1 illustrates a slit projection type of digital radiography system S in which the present invention is incorporated. A scanner 2 pivot scans an x-ray spread beam generally about a horizontal axis. A high voltage generating system 4 produces a high voltage potential across an x-ray tube 18 (see FIG. 2) necessary for the production of x-rays. A patient support 6 supports a patient under examination in the beam path such that an area of the patient's body is scanned. A pattern of x-rays emerging from the patient is detected. Information represented by the detected x-rays is processed by processing circuitry in a console, and displayed to illustrate a representation of an image of the patient's internal body structure or condition on a monitor 10. Hard copies of the images displayed on monitor 10 can be produced through the use of hard copy recorder 12 of known type.

Figure 2:
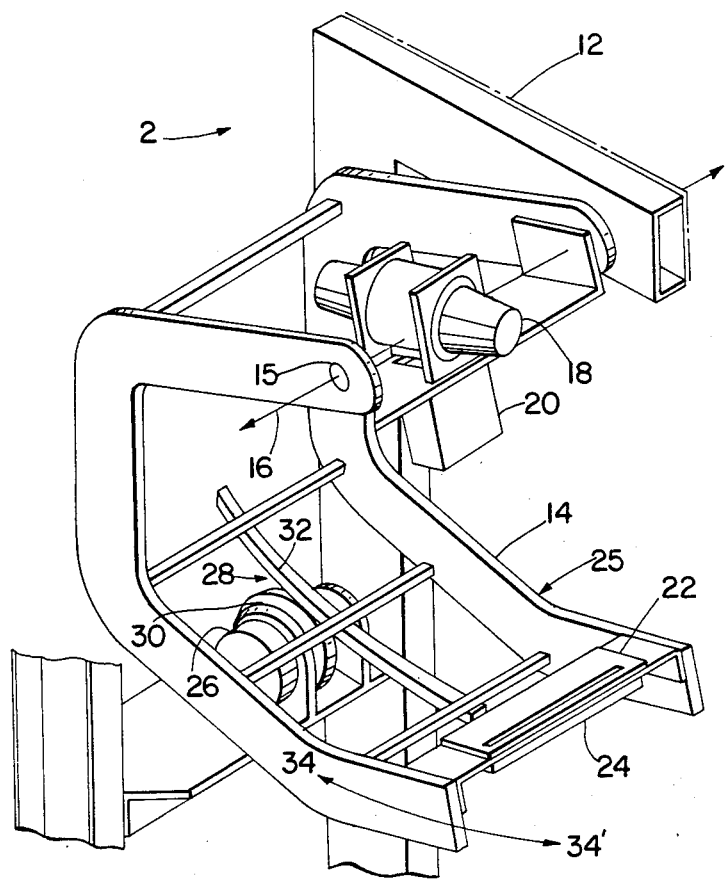
FIG. 2 is a partial, cut-away view of the scanner of FIG. 1.

With reference to FIG. 2, the scanner 2 is shown in more detail. In FIG. 2, the decorative covers have been removed and partial support structure cut-away in order to better portray and detail the scanning motion.

The scanner 2 includes a support structure 12 for supporting other components of the system. A base portion (not shown) provides rigid floor support for the support structure 12. A generally C-shaped arm 14 is journaled for rotation about a pivot shaft 15 which is attached near an outer end of support structure 12. The arm 14 rotates back and forth about a substantially horizontal arm axis 16 extending through the pivot shaft 15.

An x-ray tube 18 of known variety provides a source of radiation which is propogated through the patient. The source is mounted for pivotal motion contemporaneous with the arm 14. Tube 18 is positioned such that arm axis 16 passes through the focal spot of the tube. A foreslit collimator 20 is generally aligned with the output of the x-rays from the tube 18. An aft slot collimator 22 is also provided for collimating x-ray energy following its emergence from the subject, which subject is positioned during a study between the foreslit collimator 20 and the aft slot collimator 22.

Aligned with the aft slot collimator 22 is an image receptor 24. In the preferred embodiment, the x-ray tube, foreslit collimator, aft-slot collimator and image receptor are rigidly coupled to the arm 14 to form an arm structure 25 and which are aligned such that the x-ray spread beam emitted from the foreslit collimator 20 passes through the slot in the aft slot collimator 22 and falls upon the image receptor 24.

The image receptor 24 comprises a linear array of silicon photodiodes. This array can have one of a range of detector-to-detector spacing or "pitches" ranging from about 0.175 millimeters to about 2.0 millimeters. Lying on top of the photodiode array in the path of incident x-rays is an x-ray scintillator which converts incident x-ray photon energy to light photon energy. The light photon energy is detected by the individual photodiodes which comprise the photodiode array. Details of making and using such an image receptor are known in prior art literature, U.S. Pat. Nos. 4,626,688 to Barnes and Re. 32,164 such as in to Kruger which are hereby expressly incorporated by reference.

The individual photodiodes of the image receptor 24 each produce an analog current which is a function of the incident light photon energy which it respectively detects. Acquisition electronics (not shown) are provided for processing the analog currents produced by the photodiodes. The photodiode signals are sampled by the acquisition electronics and evaluated. Current or charge is converted to voltage, which is then amplified and converted from analog (image) information into digital information using appropriate known analog-to-digital conversion means.

A series of data buffers, multiplexers, and dedicated processing electronics, are used to prepare the data acquired by the image receptor for transfer to storage, display, or recording devices in the form of known digital image and control data. Details of the data acquisition and electronics processes are described in prior art literature, such as the following, expressly incorporated by reference: Capp, M.P. et al. "Photoelectronic Radiology Department" S.P.I.E. Vol. 314, Digital Radiography 1981, pp. 2-7.

Connected to the imaging chain is a set of leads (not shown) over which digital image and control data is passed to devices of known type, such as located in the console 8, which convert this data into viewable medical diagnostic x-ray images presented on monitors. For the system of this invention, the imaging chain is connected to CRT displays, such as at 10.

To effect scanning motion of the arm structure 25, a torque motor 26 of known type is mounted to the support structure 12. The motor 26 is operatively coupled to the arm 14 via a drive assembly 28. The drive assembly includes a drum portion 30 fixedly mounted to the rotation shaft of the motor 26, and a rib portion 32 fixedly attached to the pivotal arm 14. Engagement of the drum 30 to the rib 32 can be by friction, gearing or other suitable means. In this fashion, rotational motion of the motor shaft imparts pivotal motion to the arm structure 25. The rotational motion of the arm structure 25 causes the image receptor 24 to trace a curved path shown generally by arrows 34, 34' which lies in a substantially vertical plane. An encoder (not shown) is coupled in known fashion to the torque motor 26 and produces a signal indicating the instantaneous position of the image receptor 24 along its arcuate path. Suitable motor control circuitry (not shown) drives motor 26 to produce a torque sufficient to effect scanning motion. The encoder and control circuitry provide a closed-loop servo-system wherein scanning position and speed are accurately maintained. Details of such motor and control are well known in the art.

With reference to FIG. 3, it can be seen that when the arm structure 25 is at an equilibrium or at-rest position, the center-of-gravity of the structure identified generally as 27 will fall along a vertical line extending through the arm axis 16. When the arm structure is displaced from its at-rest position during scanning motion, the center-of-gravity rotates about the arm axis 16 and traces an arcuate path shown generally by arrows 29, 29'.

In order to compensate for gravitational torque about the arm axis during scanning motion, means is provided to impart about the arm axis a "balancing" torque equal and opposite the gravitational torque experienced during scanning motion.

The balancing torque of the system, i.e., the torque about the arm axis 16 required to overcome the gravitational influence on the arm structure 25 to effect scanning motion, is given by:

$$\tau = W R_2 \sin \alpha \quad (1)$$

where W is the weight of the arm structure, $R_1$ is the radius from the pivot point to the system center-of-gravity and $\alpha$ is the angle displaced from the vertical by the structure's center-of-gravity during scanning motion. (Note: Angular quantities such as $\tau$ and $\alpha$ are defined as positive in the clockwise direction in FIG. 3.) From equation (1) it is clear that during rotational motion of the arm structure the magnitude of the gravitational balancing torque of the system increases sinusoidally as the arm approaches the outer limits of its scanning range.

A cam 36 is mounted for rotation about a substantially horizontal cam axis 38, extending perpendicular into the plane of the paper in FIGS. 3 and 4. The cam axis 38 and the arm axis 16 are substantially parallel to one another. While in the preferred embodiment the cam axis 38 and the arm axis 16 are not co-axial, it is to be appreciated that in alternate embodiments both the cam 36 and the arm structure 25 may pivot about the same axis.

In the preferred embodiment, the cam 36 is operatively coupled to arm structure 25 such that cam 36 pivots about the cam axis 38 in response to angular motion of the arm structure 25 about arm axis 16 and vice versa. The manner and purpose of coupling is discussed in greater detail below.

The cam 36 defines a cam profile having a monotonically varying radius about its operative extent. The cam profile is developed such that the cam radius varies as a sinusoidal function of $\alpha$ about its operative extent. It then follows that if a force of proper magnitude is tangentially applied to the cam radius, the torque produced about the arm axis 16 will equal the gravitational torque of the rotating body. Assuming a constant force, the cam profile is determined by the following:

$$\text{CAM RADIUS} = \frac{R_1 * W}{F} \sin \alpha \quad (2)$$

where $R_1$ is the radius from the arm structure pivot point 16 to the center-of-gravity of the rotating structure, W is the weight of the rotating arm structure, and F is the tangential force applied to the cam radius.

A means for producing a predetermined force for application to the cam is also provided and is shown generally at 40 in FIG. 3. In the preferred embodiment, the force means 40 includes a torsion spring 42 having a relatively small spring constant. A relatively small spring constant is desirable in order to minimize the difference between maximum force and minimum force produced by the spring over its range of operation thereby providing a substantially constant force. One end of the torsion spring 42 is fixedly mounted to a shaft 43 extending through the central area of the spring. The opposite end of spring 42 is free to rotate about the shaft 43. Take-up pulley 46 is fixedly attached to the free end of spring 42 such that rotation of the pulley causes like rotation of the free end of the spring.

Coupling means 44 is used to couple the predetermined force means 40 to the cam 36 thereby transferring the predetermined force to the cam. The coupling means 44 preferably is a flexible, wire rope cable. One end portion of the cable is fixed in known fashion to the free end of the torsion spring 42 via cable take-up pulley 46. The cable is wrapped around the cable take-up pulley a number of times in order that sufficient cable length is available during scanning motion. The other end portion of the cable is fixed to the cam at the end wherein the cam radius is the greatest, generally designated at 47 (see FIG. 4). The cable is reeved about the perimeter of the cam and is received by a groove portion 48 cut into the cam periphery.

The circumference of the cable take-up pulley 46 is approximately ½ the circumference of the cam 36. This ratio allows the spring 42 to wind approximately two turns for every cam turn. This arrangement minimizes error that may be caused by nonlinearity in the spring constant.

It is to be readily appreciated that although in the preferred embodiment a torsion spring is described, any other means of producing a predetermined force is contemplated by this invention. For example, as is shown in FIG. 3A a lead weight 45 suspended against gravity would suitably provide the force required for operation of the present invention. To achieve one of the stated advantages of the present invention, the counterweight would be suspended remote from the scanner so that substantial weight is not added to the system.

As described above, the cam 36 is rotatively coupled to the arm structure 25. A drive means 48 interconnects cam 38 to arm structure 25 at a predetermined drive ratio. A drive bar arm 50 is fixedly attached to the arm structure 25 and defines a radius $R_2$ measured from the arm structure pivot axis 16. A drive pulley 54 is fixedly attached to the cam 38 and defines a radius $R_3$ measured from the cam axis 38. The circumference of the drive pulley 54 is engaged with the circumference of the drive bar arm 50 through suitable means such as friction or gearing. In this fashion rotational motion of the arm structure 25 about the arm axis 16 causes rotational motion of the cam 36 about the cam axis 38 but in an opposite direction. The radius $R_2$ is chosen to be greater than radius $R_3$ in order that limited angular motion of the arm structure 25 causes a near full rotation of the cam 36. In the preferred embodiment the drive ratio is 6:1.

By virtue of the drive means 48 and the ratio of radius $R_3$ to radius $R_2$, the torque about cam axis 38 is transferred to the arm axis 16 at the same ratio. With a 6:1 torque transfer ratio, the cam torque is 1/6 of the arm torque. With a non-unitary torque transfer ratio, equation (2) must be modified. The cam profile is now determined by the following:

$$R(\alpha) = \frac{R_3 * R_1 * W}{R_2 * F} \sin \alpha \qquad (3)$$

Where $R(\alpha)$ is the cam radius (i.e., the distance from the cam axis 38 to the point at which the coupling means, 44 is tangent to the cam) at arm angle $\alpha$, $R_3/R_2$ is the drive ratio, $R_1$ is the radius from the arm structure pivot point 16 to the center-of-gravity of the rotating structure, $W$ is the weight of the rotation arm structure, and $F$ is the tangential force applied to the cam radius. (Note: Eq. (3) is based on the approximation that the cam radius $R(\alpha)$ is perpendicular to the coupling means at the tangent point. This approximation can be seen to be quite accurate by studying FIG. 3. The slight error introduced by this assumption could be taken into account in the cam profile design, but, from a practical point of view, it complicates the design and is unnecessary.)

The invention as so for described provides gravitational counterbalance to rotating structures. However, where a spring is used to provide the predetermined force (as opposed to constant force means such as weights suspended against gravity), difficulties are encountered due to the variation in force produced by the spring during operation. The spring force is not constant, but will vary as a function of the amount of cable dispensed by the take-up pulley 46. With a purely sinusoidal cam profile as described above, variations in the torque about the cam axis 38 caused by the spring characteristics will be magnified (by the torque transfer ratio) in the torque about the arm axis 16. It is therefore desirable to modify the cam profile to substantially compensate for the spring characteristic thereby transferring about the arm axis 16 a substantially sinusoidally varying torque.

The spring force $F$ in equation (3) is represented by:

$$F(\alpha) = \qquad (4)$$
$$-K \int_{\alpha_0}^{\alpha} \sqrt{\left(\frac{dR(\alpha)}{d(\alpha)}\right)^2 + \left(\frac{R_2 * R(\alpha)}{R_3}\right)^2} \, d(\alpha) + F(\alpha_0)$$

where
  K is the spring constant,
  $\alpha$ is the angle displaced from the vertical by the structure center-of-gravity during scanning motion (defined as positive in the clockwise direction in FIG. 3)
  $R(\alpha)$ is the cam radius,
  $R_2$ is the drive bar arm radius,
  $R_3$ is the drive pulley radius, $\alpha_o$ is some reference value of $\alpha$ at which F is known.

The integral in equation (4) represents the arc length of cam circumference traversed (and length of cable dispensed or wound-up) during angular motion from $\alpha_o$ to $\alpha$. Once the spring force for a given angular position is known, [i.e., once $F(\alpha)$ is defined], equations (3) and (4) constitute a system of two equations in the two unknown functions $R(\alpha)$ and $F(\alpha)$, and can be solved to determine the cam radius profile $R(\alpha)$.

The solution to Eqs. (3) and (4) can be found iteratively using the following procedure.

Suppose the image scan arc is from $\alpha = 20$ deg to $\alpha = 40$ deg. To allow some margin on each side of the image scan arc, we may choose to design the cam to operate over the range $\alpha = 10$ deg to $\alpha = 50$ deg. Let $\alpha = 10$ deg be the "reference" angle $\alpha_o$ from which we will begin designing the cam. Select an appropriate value of spring force to be the force at this reference angle, i.e., select $F(\alpha_o)$. (The appropriate value of $F(\alpha_o)$ will depend on the weight of the scan arm, desired range of cam radii, strength and allowed range of spring force, etc.)

As a first approximation, calculate the cam profile $R(\alpha)$ from Eq. (3) using the constant spring force $F(\alpha_o)$ This will give a profile, but does not yet include corrections for the fact that the spring force varies slightly with the amount of cable dispersed.

Next, substitute the cam profile $R(\alpha)$ just calculated into Eq. (4) and calculate (the first approximation of) the spring force "profile" $F(\alpha)$. The integral in Eq. (4) can be evaluated numerically in any of a number of known ways, for example, by means of Simpsons's rule.

Next, substitute the spring force profile $F(\alpha)$ just calculated into Eq. (3) and derive a new and better approximation of the cam profile $R(\alpha)$.

Continue this iterative procedure until the cam and force profiles converge to their "true" shapes. The convergence has been found to be quite rapid, with only about five iterations required to derive sufficient accuracy for practical purposes.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A radiation scanner system comprising:

(a) an arm structure pivotally mounted to a support structure for angular motion about a substantially horizontal arm axis;
(b) means for producing a predetermined force;
(c) a radiation source;
(d) a detector mounted on said arm structure and being spaced from said source to accommodate placement of a subject therebetween;
(e) means for compensating gravitational torque about said arm axis during angular motion, said compensating means comprising:
  (i) a cam means rotatively coupled to said arm structure for pivotal motion in response to said angular motion; and
  (ii) means for engaging said cam means with said predetermined force; and
(f) means electrically connected to the detector for producing an image corresponding to radiation incident on said detector.

2. The system of claim 1 wherein said engaging means comprises a portion of a cable and said predetermined force producing means comprises a spring.

3. The system of claim 2 wherein said cam means defines a profile having a monotonically varying radius out its operative extent, said radius varying as a function of gravitational torque about the arm axis and as a function of spring force.

4. The system of claim 1 wherein said compensating means comprises:
(a) means for producing a predetermined force;
(b) a cam operatively coupled to said arm structure for pivotal motion about a substantially horizontal cam axis in response to said angular motion, said cam defining a profile having a monotonically varying radius about its operative extent; and
(c) means coupled to the cam for transferring said predetermined force to said cam.

5. The system of claim 4 wherein said cam radius varies sinusoidally.

6. The system of claim 1 wherein said compensating means comprises:
(a) a cam mounted for pivotal motion about a substantially horizontal cam axis and operatively coupled to said force producing means for converting said predetermined force to a torque about said cam axis; and
(b) means for rotatively coupling said cam to said arm structure for transferring said torque about said cam axis to a torque about said arm axis.

7. The system of claim 8 wherein said coupling means defines a torque transfer ratio.

8. The system of claim 7 wherein said torque transfer ratio is 6:1.

9. The system of claim 6 wherein the means for providing a predetermined force comprises a spring.

10. The system of claim 9 wherein said spring is of the torsion type.

11. The system of claim 11 wherein said cam means defines a profile having a substantially sinusoidally varying radius modified to compensate for variation in spring force.

12. The system of claim 6 wherein the means for producing a predetermined force comprises a weight suspended against gravity.

13. In a radiation scanner system comprising a source of radiation, a counterbalance comprising;
(a) a support structure;
(b) an arm structure;
(c) means for pivotally mounted said arm structure to said support structure for rotation about a substantially horizontal arm axis;
(d) means for producing a predetermined force;
(e) a cam means mounted for pivotal motion about a substantially horizontal cam axis and coupled to said force producing means for converting said predetermined force to a first torque about said cam axis; and
(f) means for coupling said cam means to said arm structure for transferring said first torque about said cam axis to a second torque about said arm axis at a predetermined ratio.

14. The system of claim 13 wherein said predetermined force producing means comprises a torsional spring.

15. A counterbalance system in a rotating diagnostic imaging system comprising a radiation source for use in counteracting gravitational torque about a pivot axis comprising;
(a) a means for producing a predetermined force;
(b) cam means mounted for pivotal motion about a cam axis and coupled to said force producing means for converting said predetermined force into a first torque about said cam axis; and
(c) means for coupling the cam means to the rotating diagnostic imaging equipment whereby said first torque about said cam axis is transferred to a second torque about said pivot axis.

16. The system of claim 15 wherein said predetermined force producing is a spring.

17. The system of claim 16 wherein said spring is a torsional spring.

18. The system, of claim 17 wherein said cam means defines a profile having a substantially sinusoidally varying radius modified to compensate for variation in spring force.

19. The system of claim 15 wherein said predetermined force producing means is a weight suspended against gravity.

20. The system of claim 15 wherein said cam means comprises a cam defining a profile having a monotonically varying radius about its operative extent.

21. The system of claim 20 wherein said cam radius varies sinusoidally.

* * * * *

UNITED STATES PATENT AND TRADEMARK OFFICE
CERTIFICATE OF CORRECTION

PATENT NO. : 4,813,064

DATED : Mar. 14, 1989

INVENTOR(S) : David Jackson, III; Dale A. Havel

It is certified that error appears in the above-identified patent and that said Letters Patent is hereby corrected as shown below:

Column 3, line 51, change "resent" to --present--;

Column 4, line 48, change "such as in to" to --such as to--;

Column 5, line 51, change "$R_2$" to --$R_1$--.

Signed and Sealed this

Twenty-sixth Day of December, 1989

Attest:

JEFFREY M. SAMUELS

Attesting Officer     Acting Commissioner of Patents and Trademarks